United States Patent [19]
Holder

[11] Patent Number: 5,795,381
[45] Date of Patent: Aug. 18, 1998

[54] SIO PROBE FOR REAL-TIME MONITORING AND CONTROL OF OXYGEN DURING CZOCHRALSKI GROWTH OF SINGLE CRYSTAL SILICON

[75] Inventor: John D. Holder. St. Louis. Mo.

[73] Assignee: MEMC Electrical Materials, Inc.. St. Peters. Mo.

[21] Appl. No.: 711,085

[22] Filed: Sep. 9, 1996

[51] Int. Cl.$^6$ .................................................. C30B 15/00
[52] U.S. Cl. .............................. 117/14; 117/11; 117/13; 117/15; 117/20; 423/350
[58] Field of Search ........................ 75/10.5; 423/350. 423/325; 373/22; 117/11–20

[56] References Cited

U.S. PATENT DOCUMENTS

| 4,010,064 | 3/1977 | Patrick et al. | 156/617 SP |
| 4,040,895 | 8/1977 | Patrick et al. | 156/618 |
| 4,344,815 | 8/1982 | Cazarra et al. | 156/601 |
| 4,400,232 | 8/1983 | Ownby et al. | 156/601 |
| 4,436,577 | 3/1984 | Federick et al. | 156/617 |
| 4,511,428 | 4/1985 | Ghosh et al. | 156/601 |
| 4,545,849 | 10/1985 | d'Aragona | 156/617 SP |
| 4,591,409 | 5/1986 | Ziem et al. | 156/605 |
| 4,997,474 | 3/1991 | Dosaj et al. | 75/10.5 |
| 5,131,974 | 7/1992 | Oda et al. | 156/601 |
| 5,178,720 | 1/1993 | Frederick | 156/618.1 |
| 5,269,875 | 12/1993 | Sonokawa et al. | 156/605 |
| 5,386,118 | 1/1995 | Kitagawara et al. | 250/338.1 |

OTHER PUBLICATIONS

T. Carlberg "Calculated Solubilities of Oxygen in Liquid and Solid Silicon" J. Electrochem. Soc.: Solid–State Science & Technology, vol. 133, No. 9, (9/1986) pp. 1940–1942.

Z. Liu et al. "On the Mechanism of Oxygen Content Reduction by Antimony Doping of Czochralski Silicon Melts" J. Electrochem Soc.. vol. 138. No. 5 (5/1991) pp. 1488–1492.

Z. Liu et al. "The Influence of Dopants on the Reaction Between Liquid Silicon and Silica" J. Electrochem. Soc.. vol. 139, No. 3 (3/1992) pp. 844–849.

A. Seidl et al. "Development of an Electrochemical Oxygen Sensor for Czochralski Silicon Melts" J. Electrochem. Soc. vol. 141, No. 9 (9/1994) pp. 2564–2566.

F. Shimura "Semiconductor Silicon Crystal Technology-"Academic Press, Inc., San Diego, CA (1989) pp. 160–167.

K-W Yi et al. "Asymmetric Distribution of Oxygen Concentration in the Si Melt of a Czochralski System" J. Electrochem. Soc.. vol. 143, No. 2 (2/1996) pp. 722–725.

Primary Examiner—Jeffrey Stucker
Attorney, Agent, or Firm—Senniger. Powers. Leavitt & Roedel

[57] ABSTRACT

Methods for quantifying, in near real-time, the amount of silicon oxide (SiO) volatilized from a pool of molten silicon such as a Czochralski silicon melt and present in the atmosphere over the melt are disclosed. A preferred method includes reacting a gas sample containing SiO withdrawn from the atmosphere over the molten silicon with a reactant to form a detectable reaction product, determining the amount of reaction product formed, and correlating the determined amount of reaction product to the amount of SiO present in the atmosphere. The quantification of SiO is used for monitoring and/or controlling the amount of oxygen in the molten silicon or the oxygen content in single crystal silicon being drawn from the molten silicon. A SiO reaction probe and a system using the probe for monitoring and/or controlling oxygen are also disclosed.

30 Claims, 12 Drawing Sheets

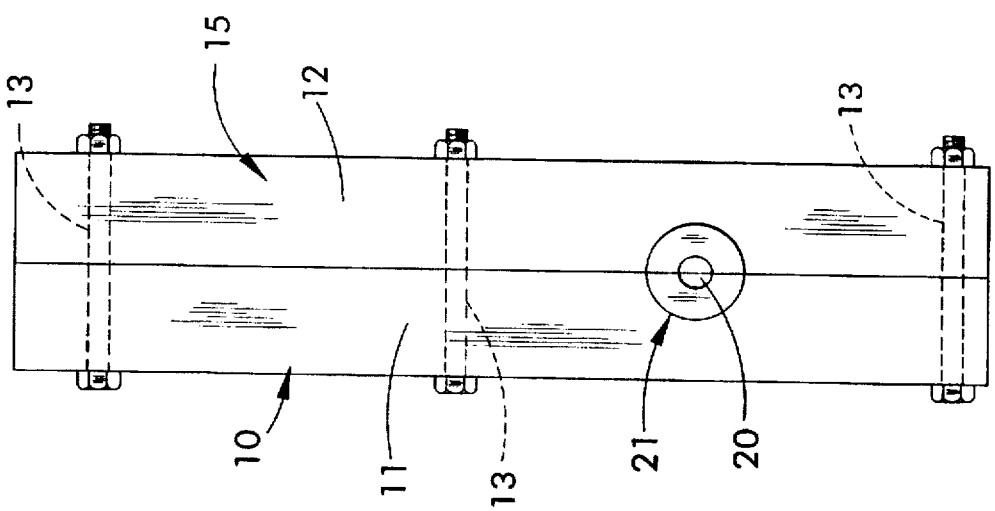
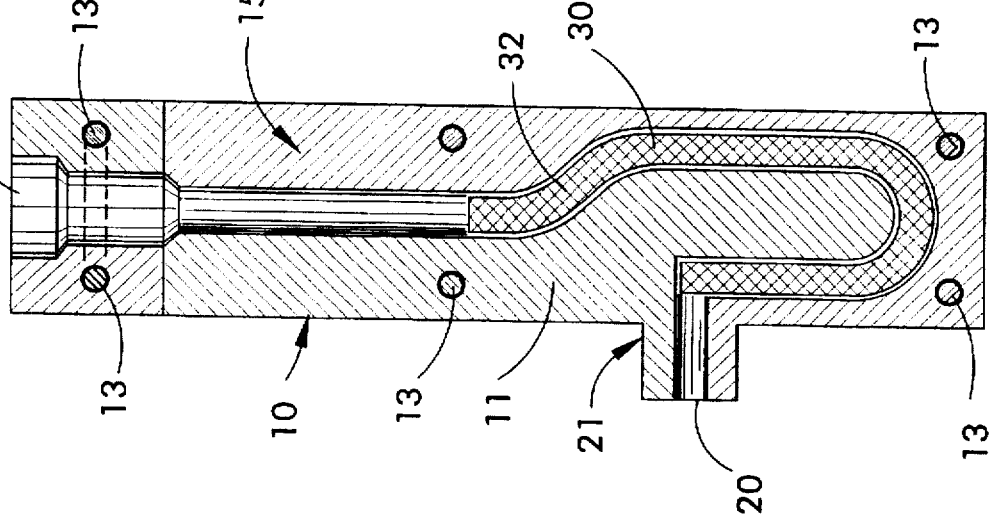
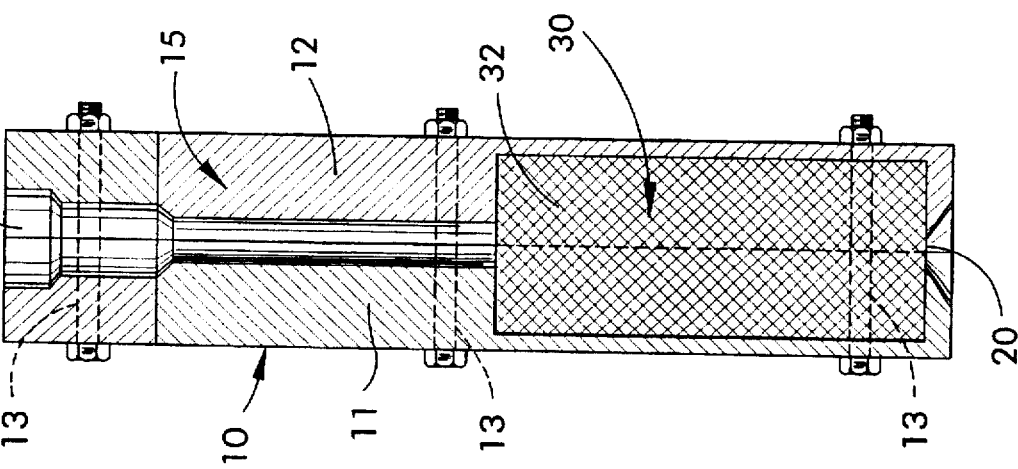

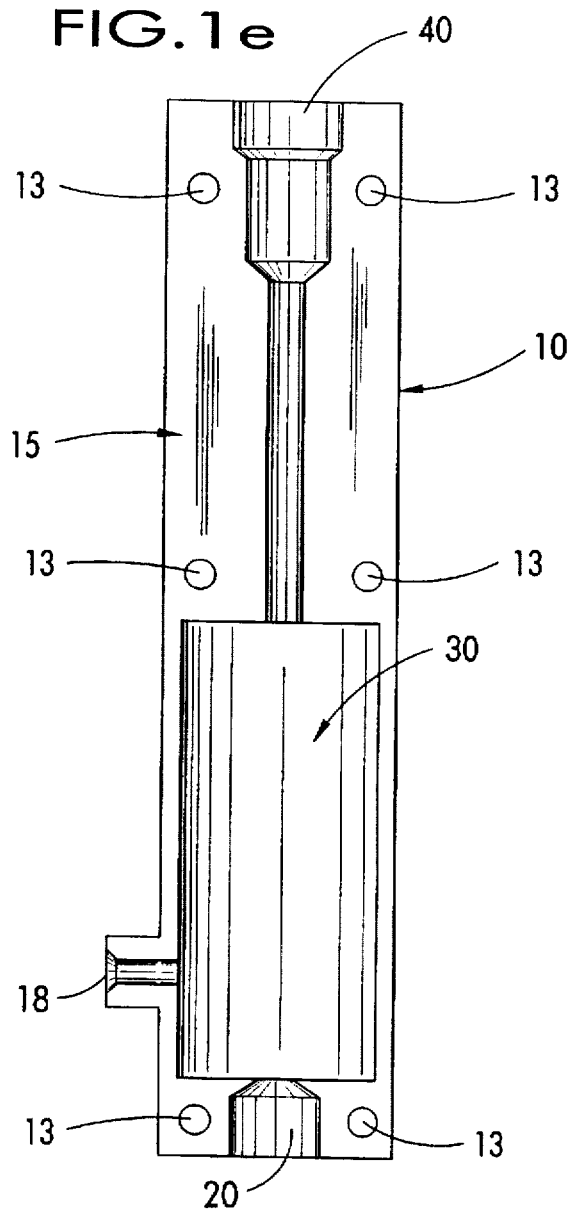

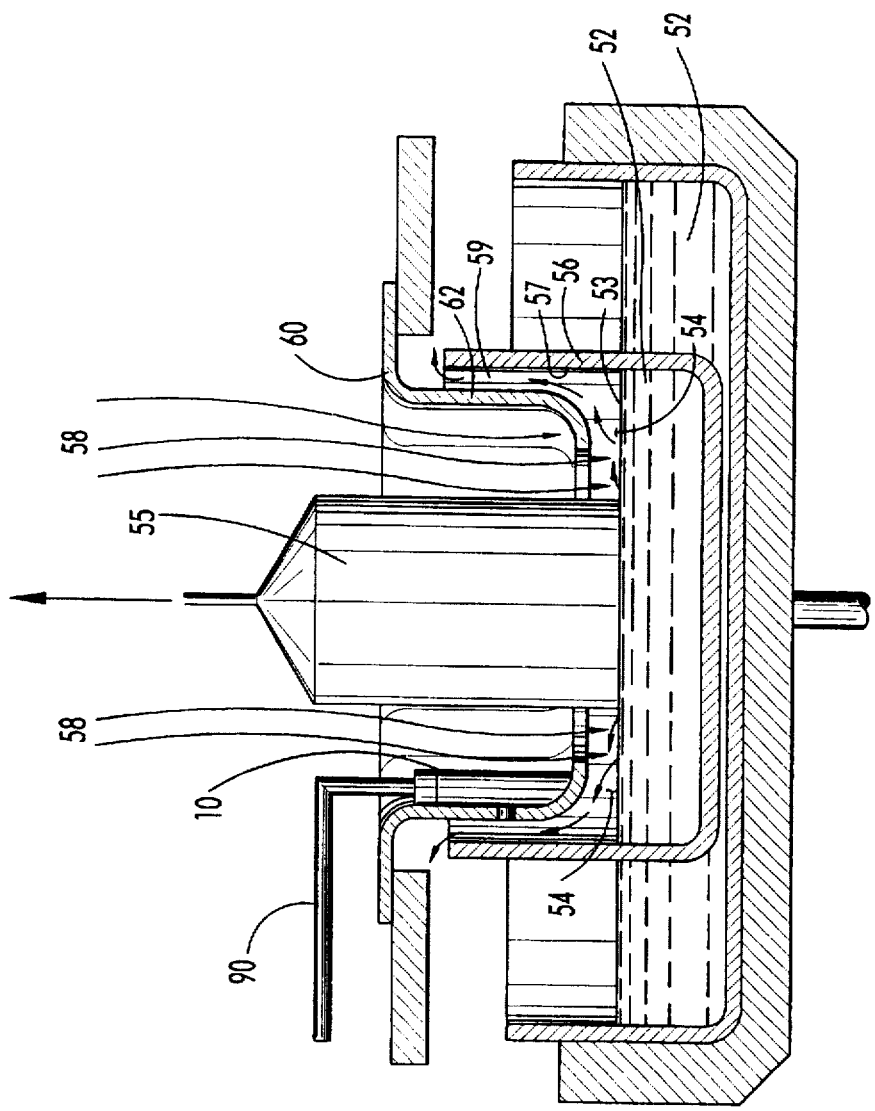

SIO PROBE FOR REAL-TIME MONITORING AND CONTROL OF OXYGEN DURING CZOCHRALSKI GROWTH OF SINGLE CRYSTAL SILICON

BACKGROUND OF THE INVENTION

The present invention generally relates to the production of single crystal silicon, and specifically, to an apparatus and method for real-time monitoring and control of the oxygen content of single crystal silicon grown by the Czochralski method.

Most single crystal silicon used for microelectronic circuit fabrication is prepared by the Czochralski (CZ) method. In this process, a single crystal silicon ingot is produced by melting polycrystalline silicon in a fused quartz crucible, dipping a seed crystal into the molten silicon, withdrawing the seed crystal to initiate single crystal growth, and growing the single crystal under process conditions controlled to maximize the performance characteristics of the single crystal ingot. The oxygen content of the resulting silicon crystal ingot is particularly important. While uniformly-distributed oxygen has favorable effects on device fabrication, non-uniform axial and/or radial oxygen distribution is detrimental to product uniformity and throughput.

The quartz crucible is the primary source of oxygen in a Czochralski single crystal silicon ingot. At the melt temperature of polycrystalline silicon, the inner surface of the $SiO_2$ crucible dissolves into the silicon. Some of the oxygen in the silicon melt evaporates from the free surface of the melt as volatile SiO. The oxygen in the silicon melt also becomes incorporated into the growing crystal at the crystal/melt interface. The oxygen content of the silicon crystal typically decreases over the length of the ingot, the decrease being associated with a corresponding decrease in the area of contact between the inner surface of the crucible and the melt as the melt volume becomes depleted during crystal growth.

While a variety of approaches are known for controlling the oxygen content and distribution in single crystal silicon, present approaches lack a real-time mechanism for determining and/or monitoring the oxygen content in the growing crystal. Oxygen content and distribution is typically evaluated after crystal growth has been completed. Exemplary post-crystal-growth methods for determining oxygen content include FTIR spectroscopic techniques and resistivity-shift methods, such as are taught in U.S. Pat. No. 's 5,386,118 to Kitagawara et al. and 4,344,815 to Cazarra et al., respectively. However, where a sample is not taken from an area of the ingot affected by a process upset, a change in oxygen content may go undetected.

Moreover, the art lacks a viable method for making changes to the oxygen-affecting process parameters based on changes in real-time oxygen content. Presently, a particular set of process conditions are controlled based on the experience gained from prior multiple independent crystal pulls. Pre-programmed control scenarios have been developed based on such post-growth analyses to minimize oxygen variation. However, such approaches do not account for unanticipated peturbances such as abrupt changes in melt convection pattern. These approaches are also not practical for developing new or changed oxygen control schemes.

To date, real-time approaches for sensing or measuring oxygen content have focused on electrochemical methods. For example, U.S. Pat. No. 4,400,232 to Ownby et al. discloses an electrochemical sensor for determining the partial pressure of oxygen in the atmosphere above the silicon melt, in which a solid thoria-yttria electrolyte is employed. More recently, Seidl et al. have disclosed an electrochemical oxygen sensor used during crystal growth in which the electrochemical potential between a CaO-stabilized $ZrO_2$ electrode and a graphite electrode in contact with the melt are correlated to oxygen concentration in the melt. *Development of an Electrochemical Oxygen Sensor for Czochralski Silicon Melts*, J. Electrochem. Soc., Vol 141, No. 9 (September, 1994). Yi et al. disclose an analogous approach. *Asymmetric Distribution of Oxygen Concentration in the Si Melt of a Czochralski System*, J. Electrochem. Soc., Vol 143, No. 2 (February, 1996). However, electrochemical systems generally suffer from several drawbacks, including being limited to location specific measurement and being temperature dependent. Moreover, the systems having electrodes in direct contact with the melt are not practical for commercial application, due to potential contamination of the melt from the electrodes and due to inaccuracies which approach the level of oxygen being measured.

SUMMARY OF THE INVENTION

It is therefore an object of the present invention to provide an apparatus and method for real-time measurement and control of the oxygen content in a Czochralski silicon melt and/or in a single crystal silicon ingot being grown therefrom by the Czochralski method. It is also an object to accurately quantify changes in crystal oxygen content while the crystal is being grown.

Briefly, therefore, the present invention is directed to a method for determining the amount of SiO present in an atmosphere over a pool of molten silicon. In this method, SiO present in the atmosphere is reacted with a reactant to form a detectable reaction product. The reaction preferably occurs in a sampling/reaction probe after drawing a sample of the atmosphere into the probe. The amount of reaction product formed is determined and correlated to the amount of SiO present in the atmosphere.

The invention is also directed to methods for determining the amount of oxygen in a pool of molten silicon. According to a general method, the amount of SiO present in an atmosphere over the pool of molten silicon is quantified and correlated to the amount of oxygen in the molten silicon. In a more specific method, a sample containing SiO is drawn from the atmosphere over the molten silicon and the SiO present in the sample is reacted with a reactant to form a detectable reaction product. The amount of reaction product formed is determined and correlated to the amount of oxygen in the pool of molten silicon.

The invention is directed as well to methods for determining, in near real-time, the oxygen content in a single crystal silicon ingot being drawn from a pool of molten silicon. In one method, the amount of SiO present in an atmosphere over the pool of molten silicon is quantified and correlated to the oxygen content in the single crystal silicon ingot. In a more specific method, a sample containing SiO is drawn from the atmosphere over the pool of molten silicon and reacted with a reactant to form a detectable reaction product. The amount of reaction product formed is determined and correlated to the oxygen content in the single crystal silicon ingot.

The invention is further directed to a method for controlling the oxygen content in a single crystal silicon ingot being drawn from a pool of molten silicon. The control is preferably effected in real time or near-real time. In a general method therefor, the amount of SiO present in an atmosphere over the pool of molten silicon is quantified while the silicon ingot is being drawn, and at least one process condition that affects the oxygen content in the silicon ingot is changed. The sense (e.g. increase or decrease) and magnitude of the change in the process condition being controlled is based on the quantified amount of SiO present in the atmosphere. Another method therefor comprises withdrawing a sample containing SiO from an atmosphere over the pool of molten silicon, and reacting SiO present in the sample with a reactant to form a detectable reaction product. The amount of reaction product formed is then determined and at least one process condition that affects the oxygen content in the silicon ingot is changed. The sense and magnitude of the change to the process condition are correlated to the determined amount of reaction product.

The invention is directed, moreover, to a probe suitable for use in a system for determining or controlling, in near-real time, the amount of SiO present in an atmosphere over a pool of molten silicon, the amount of oxygen in the molten silicon or the oxygen content of a single crystal silicon ingot drawn from the molten silicon, and particularly, suitable for reacting SiO present in a gas sample withdrawn from the atmosphere over the molten silicon with a reactant to form a detectable reaction product. The probe comprises a reaction chamber and inlet and outlet ports in fluid communication with the chamber. The inlet port is adapted for fluid communication with the atmosphere for withdrawing a sample containing SiO from the atmosphere into the reaction chamber, which is defined in a body of the probe. The probe body is made of a material having a melting point sufficient to withstand the environment of the atmosphere above the molten silicon and is preferably non-contaminating to the molten silicon when positioned over the pool of molten silicon and/or to the silicon ingot ultimately drawn therefrom. During use, and in a pre-loaded embodiment prior to use, the probe further comprises a reactant material contained within the chamber. The reactant material is capable of reacting with SiO present in the sample to form a detectable reaction product. The outlet port is in fluid communication with the chamber and is adapted for fluid communication with a detector for determining the amount of reaction product formed.

The invention is also directed to a system for use in determining or controlling, in near-real time, the amount of SiO present in an atmosphere over a pool of molten silicon contained within a crucible, the amount of oxygen in the molten silicon or the oxygen content of a single crystal silicon ingot drawn from the molten silicon according to the Czochraski method. The system includes a SiO reaction probe, as described above, located within a Czochraski crystal puller in the atmosphere over the pool of molten silicon for reacting SiO present in a gas sample withdrawn from the atmosphere with a reactant to form a detectable reaction product. The probe is, during use, pre-loaded or continuously fed with a reactant material which is capable of reacting with SiO present in the sample drawn into the chamber through the inlet port to form a detectable reaction product. The system also includes a detector for determining the amount of reaction product formed.

Other features and objects of the present invention will be in part apparent to those skilled in the art and in part pointed out hereinafter.

BRIEF DESCRIPTION OF THE DRAWINGS

FIG.'s 1(a) through 1(e) are views of alternative configurations of a SiO reaction probe. FIG. 1(a) is a schematic cross-sectional view of one configuration suitable for use with a solid reactant. FIG. 1(b) is a schematic cross-sectional view of an alternative configuration for use with a solid reactant. FIG. 1(c) is a side-view of the configuration shown in FIG. 1(b). FIG. 1(e) is a schematic cross-sectional view of a configuration suitable for use with a gaseous or atomized fluid reactant.

FIG.'s 2(a) through 2(c) are section views of a Czochralski crystal puller. FIG. 2(c) shows a continuous puller with the probe of FIG. 1(b).

Figure 1D:
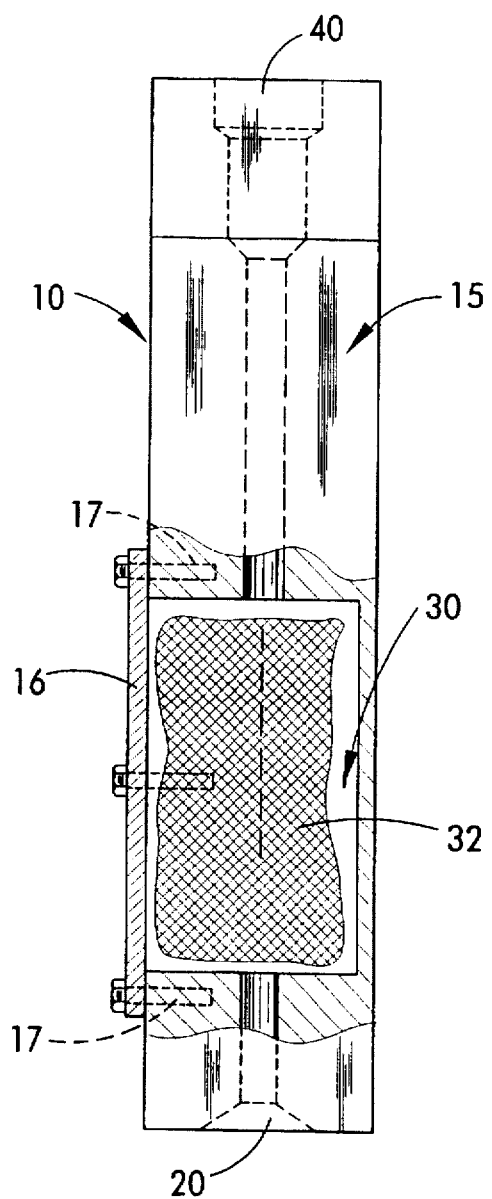
FIG. 1(d) is a schematic cross-sectional view of another alternative configuration for use with a solid reactant.

The invention is described in further detail below with reference to the figures, in which like items are numbered the same in the several figures.

DETAILED DESCRIPTION OF THE INVENTION

The present invention employs a novel approach for monitoring and controlling oxygen content in single crystal silicon being drawn from a pool of molten silicon in a Czochralski-type crystal puller—real-time quantification of the amount of volatile silicon oxide, SiO, present in the atmosphere above the melt. The amount of SiO over a pool of molten silicon such as a Czochralksi silicon melt is quantitatively related to several practically important parameters, including the evaporation rate of SiO from the melt surface, the amount of oxygen in the molten silicon, and the oxygen content of the silicon crystal being drawn from the molten silicon. Hence, quantifying the amount of SiO over the molten silicon finds application in determining, detecting changes in and controlling these parameters. The ability to monitor and control the oxygen content of the crystal in real-time or near real-time provides for significantly improved axial uniformity. However, because SiO volatilized from the melt surface is highly unstable and typically recombines as $SiO_2$ and Si at temperatures of about 1200° C., quantifying the amount of SiO present in the atmosphere over the melt has not heretofore been proposed for use in such applications.

The amount of SiO present in the atmosphere over a pool of molten silicon is, in a preferred embodiment, quantified by withdrawing a gas sample which contains SiO from the atmosphere over the molten silicon, reacting SiO present in the sample with a reactant to form a detectable reaction product, determining the amount of the reaction product formed and correlating the determined amount of reaction product to the amount of SiO present in the atmosphere over the molten silicon. Because the SiO can be reacted and the amount of the resulting reaction product can be quantified rapidly, the quantification of SiO may be carried out in near real-time. As used herein, reference to an "amount" (e.g. of SiO or of the reaction product formed) is intended to include not only absolute amounts (moles, weight, etc), but also relative amounts (concentrations, mole fractions, mole ratios, etc) and temporal-based amounts (mass flow rates, mass fluxes, etc). Moreover, a quantified or determined amount may be expressed as a numerical value or a physical representation thereof (e.g. an electrical current or voltage signal) that corresponds, either directly or in quantitatively related terms (e.g. proportional, logarithmic, exponential, etc.), to the determined amount.

SiO present in a gas sample drawn from the atmosphere over a pool of molten silicon is most preferably reacted with carbon to form silicon carbide and gaseous carbon monoxide according to the reaction:

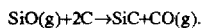

$$SiO(g) + 2C \rightarrow SiC + CO(g).$$

Other carbon-containing materials, such as carbon dioxide and hydrocarbons (e.g. methane), are also particularly suitable for use as reactants:

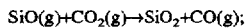

$$SiO(g) + CO_2(g) \rightarrow SiO_2 + CO(g);$$

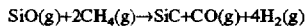

$$SiO(g) + 2CH_4(g) \rightarrow SiC + CO(g) + 4H_2(g)$$

Suitable reactants may also include other materials that are capable of reacting with SiO present in the gas sample withdrawn from the atmosphere over the molten silicon to form detectable and quantifiable reaction products. While the phase state of the reactant (solid, liquid, gas) is not narrowly critical, the reactant is preferably supplied as a solid reactant and in a form which maximizes the reactant surface area to which SiO is exposed. In the preferred reaction, graphite wool is used as the reactant. Moreover, while the extent of conversion (ie, reaction yield) is not narrowly critical, the reaction converting SiO to a detectable reaction product preferably has consistent, reproducible yields. Fractional yields of less than 100% are, as discussed below, accounted for in the various applications of the invention by using comparative values of the amount of SiO or by calibrating the determined amount of SiO against known standards or against empirically-determined data. The reaction of SiO with graphite is preferably effected at temperatures greater than about 1000° C. and at pressures equal to or greater than about 10 torr (about 1,333 Pa). While the particular pressure above this value is not narrowly critical, a preferred pressure ranges from about 10 torr (about 1,333 Pa) to about 300 torr (about 4×10⁴ Pa). Under these conditions, a complete (100%) temperature-independent yield is achieved. In the general case, the resulting reaction products are quantitatively detectable and preferably do not undergo further reaction. However, the present invention includes reaction schemes in which a direct reaction product subsequently undergoes one or more further reactions to form a secondary (or tertiary, etc.) reaction product. Preferably, at least one reaction product is a gaseous reaction product which is detectable and which does not condense at or above ambient temperature. Carbon monoxide gas is a most preferred reaction product.

Referring to FIG. 1(a), the conversion of SiO according to the aforementioned reactions is preferably effected in a reaction probe 10. The probe 10 comprises a reaction chamber 30 defined in a body 15 of the probe 10, an inlet port 20 in fluid communication with the chamber 30 and adapted for fluid communication with the atmosphere over the molten silicon for withdrawing a gas sample containing SiO from the atmosphere into the chamber 30, and an outlet port 40 in fluid communication with the chamber 30 and adapted for passing gaseous reaction products and unreacted gasses out of the chamber 30, and in a preferred embodiment, to a detector for determining the amount of reaction product formed. The shape or configuration of the chamber 30 and the relative location of the inlet port 20, chamber 30 and outlet port 40 are not narrowly critical. FIGS. 1(b) and 1(c) depict an alternative design for a reaction probe 10 having a side-entry inlet port 20 which is connected to a hook-shaped reaction chamber 30 by an inlet channel 21. As discussed below, either of the probe designs depicted in FIGS. 1(a) and 1(b) may be preferred, depending on the particular application in which the probe 10 is being used. Other probe designs could also be used.

The reaction probe 10 also preferably includes means for supplying a reactant 32 in the chamber 30. Referring to FIGS. 1(a) through 1(c), where a solid reactant will be used in the chamber 30, the body 15 of the probe 10 is preferably a two-piece body comprising a first portion 11 and a second portion 12 which together define the chamber 30. The first and second portions 11, 12 are separably fastened to each other with fasteners 13 to allow the probe 10 to be alternatively disassembled to supply a reactant in the chamber 30 and reassembled for use as described herein. FIG. 1(d) shows an alternative means for supplying a reactant in the chamber 30, in which the probe 10 includes an access cover 16. The access cover 16 is fastened to the body 15 by fasteners 17, and is capable of being opened and/or removed to allow access to the reaction chamber 30. Referring to FIG. 1(e), where a fluidized solid, a liquid, an atomized liquid or gaseous reactant will be used in the chamber 30, the reactant may be supplied in the chamber 30 by means of a reactant port 18 in fluid communication with the chamber 30 and adapted for fluid communication with a reactant source to admit the reactant from the source into the chamber 30. In an alternative, less preferred embodiment, the reaction probe 10 could be used in a disposable manner with a preloaded reactant and without any means for resupplying reactant in the chamber 30, once the preloaded reactant has been consumed. The probe body 15 is preferably made of a material that can withstand the high-temperature environment in the hot zone of a Czochralski-type crystal puller, and particularly, in the atmosphere directly over and in the near-vicinity of the molten silicon melt. For example, the material of which the body 15 is made has a melting point greater than the melting point of silicon and more preferably greater than about 1500° C. The material of which the body 15 is made should also be substantially non-contaminating to the molten silicon when positioned over the pool of molten silicon. Graphite is a preferred material, particularly where SiO is being reacted with carbon. Other materials such as quartz, refractory metals (e.g. molybdenum, tungsten), etc., are also suitable.

Figure 2A:
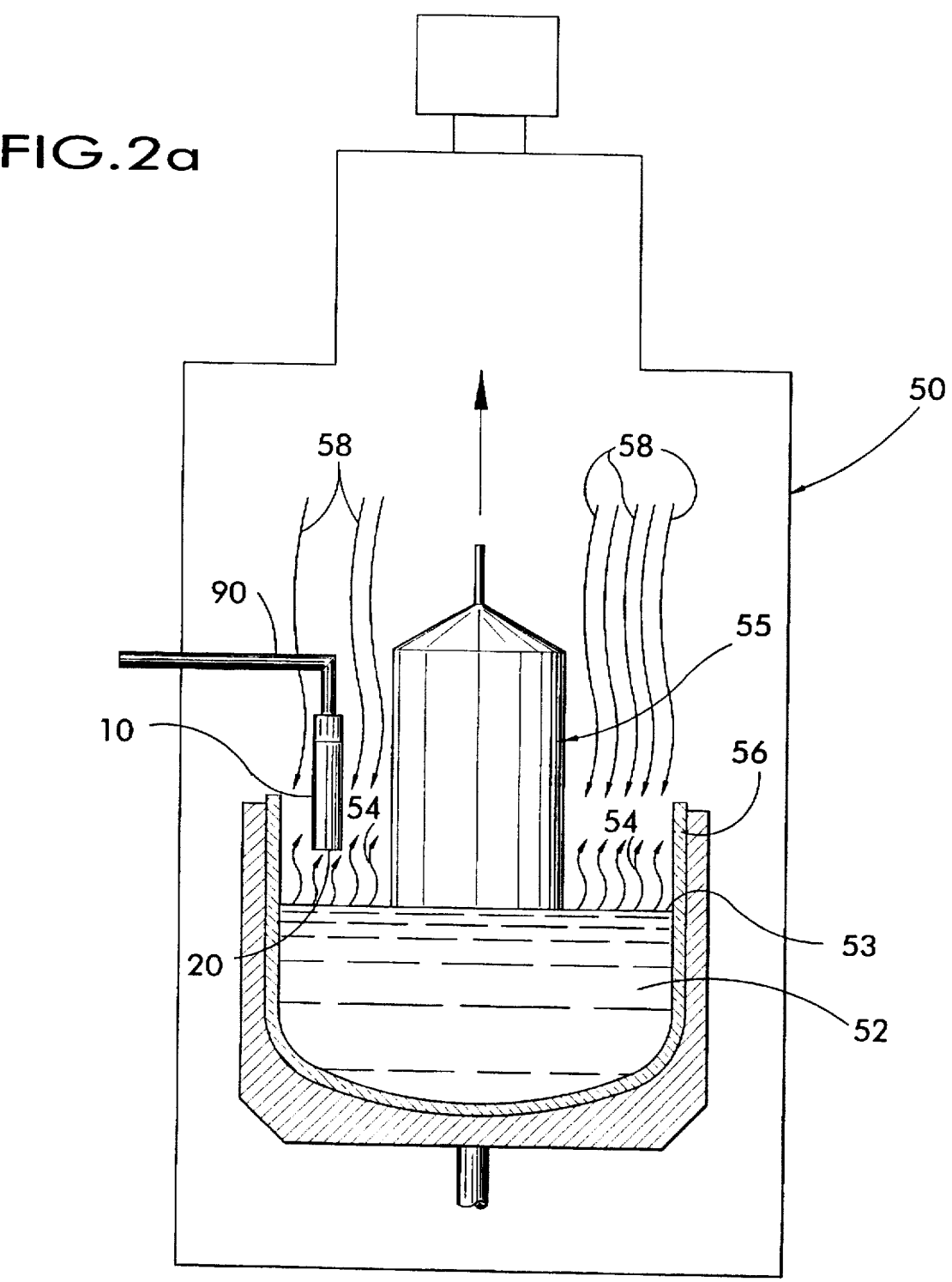
FIG. 2(a) shows a batch puller with the SiO probe of FIG. 1(a).
Figure 2B:
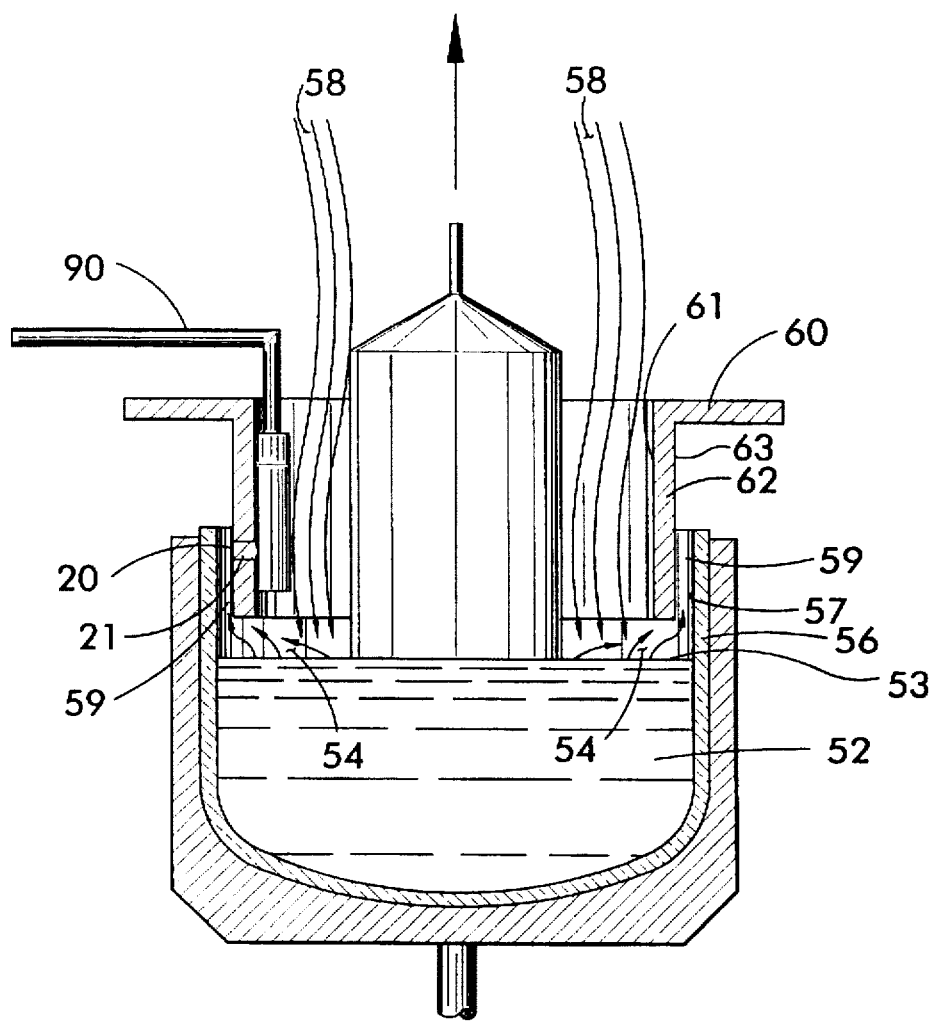
FIG. 2(b) shows a batch puller with a purge tube and the SiO probe of FIG. 1(b).

With reference to FIGS. 2(a) through 2(c), the probe 10 is preferably located within the crystal puller 50 in the atmosphere above the surface 53 of the molten silicon 52. While the exact location of the probe 10 over the melt surface 53 is not narrowly critical, the probe 10 should be positioned in sufficiently close vertical proximity to the melt surface 53 to allow for conversion of volatile SiO to a stable reaction product without substantial SiO recombination. The radial positioning of the probe 10 may slightly influence the quantification of SiO, because the concentration of volatile SiO 54 at the melt surface 53 may vary slightly between axially positions closer to the crystal 55 as compared to positions closer to the crucible 56. Because of the correlation between the amount of SiO quantified and the concentration of SiO in the melt 52, quantifying the amount of volatile SiO 54 at various radial positions may be used to study the radial variations in the SiO concentration in the silicon melt 53. For this type of application, reaction probes 10 of the design depicted in FIG. 1(a) are preferred. In the general case, however, the effect of radial variations in SiO concentration is preferably minimized by using the alternative probe design depicted in FIG. 1(b) in conjunction with a purge tube 60, as shown in FIG. 2(b). An inert purge gas 58 such as argon preferably flows down the center of the crystal puller 50 over the growing silicon ingot 55 and is peripherally constrained by the inner surface 61 of the vertical wall 62 of the purge tube 60. The purge gas 58 mixes with SiO in the atmosphere above the melt surface 53, and the resulting mixture flows peripherally outward and then upward through an annular region 59 defined by the outside surface 63 of the purge-tube vertical wall 62 and the inner wall surface 57 of the crucible 56. The annular region 59 through which the SiO/inert gas mixture flows is referred to hereinafter as the purge channel 59. In this configuration, the probe 90 is preferably positioned such that a gas sample containing SiO is drawn into the inlet port 20 of the probe 10 from the well-mixed gas mixture in the purge channel 59. In a most preferred embodiment, the probe 10 is situated adjacent the inner surface 61 of the purge tube vertical wall 62 with inlet channel 21 of the probe 10 inserted through the purge tube 60 to allow its inlet port 20 to be in fluid communication with the gas-mixture in the purge channel 59. A similar set up may be used in a continuous Czochralski system. (FIG. 2(c)). By sampling the gas mixture in the purge channel 59, radial variations in SiO concentration are physically averaged by mixing. While a single probe 10 is generally sufficient, the use of multiple probes 10 is within the scope of the present invention.

After the gas sample containing SiO is reacted to form one or more reaction products, the amount of at least one of the resulting reaction product(s) is determined using a suitable detector. While the reaction product detected and quantified is preferably a gaseous reaction product (e.g. $CO(g)$, $H_2(g)$, etc.), a solid reaction product (e.g. SiC) may also be quantitatively detected. Moreover, the exact location of the detector is not narrowly critical. The present invention encompasses detectors located within the crystal puller pressure boundary as well as detectors located external thereto.

Figure 3:
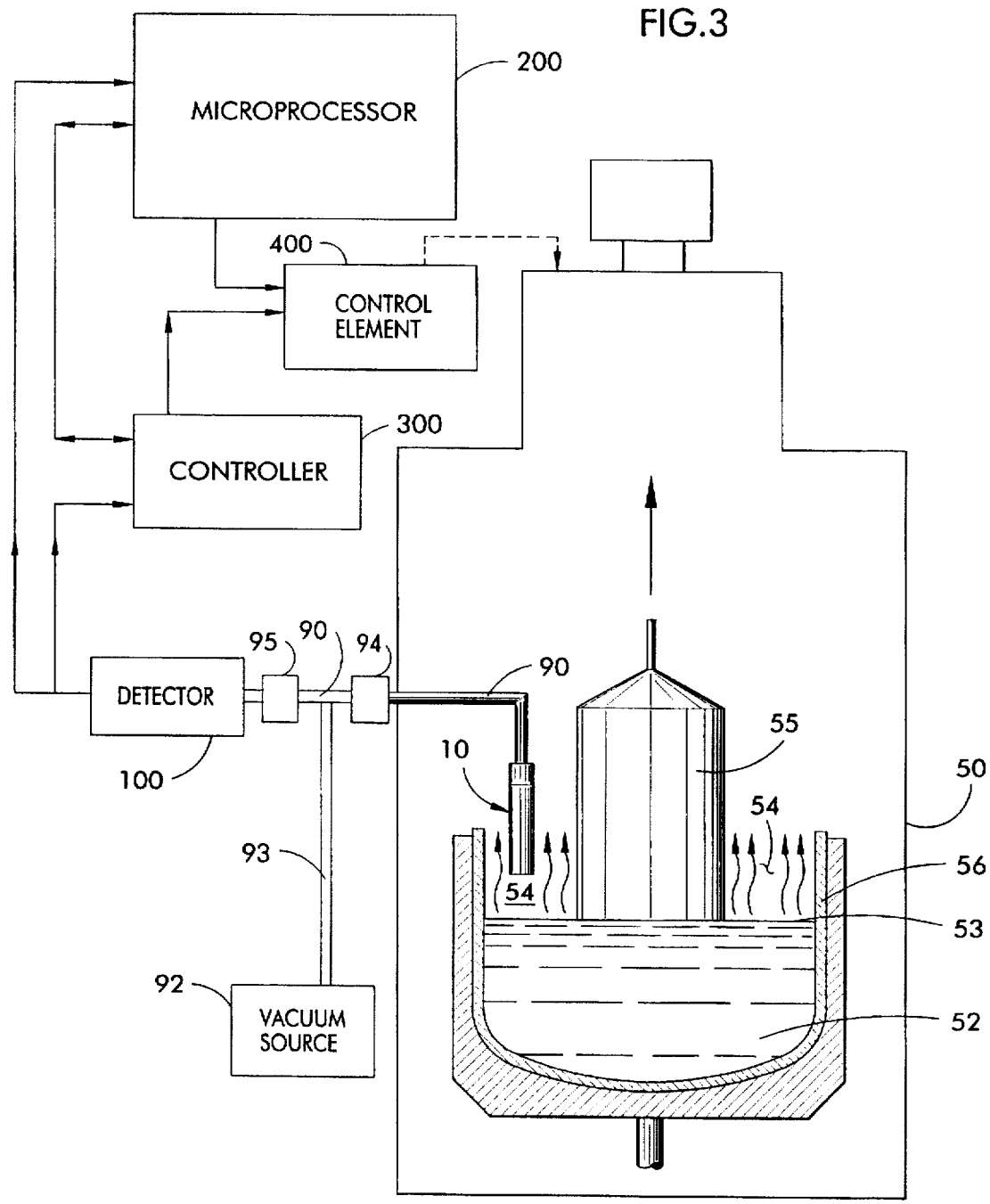
FIG. 3 is schematic diagram of a system for quantifying, monitoring and/or controlling the oxygen content of the melt or crystal, including a section view of a Czochralski crystal puller.

Referring to FIG. 3, the amount of a gaseous reaction product formed in the probe 10 from a gas sample containing SiO is preferably determined in a detector 100 located outside of (ie, external to) the crystal puller 50. A mixture of unreacted gasses (e.g. inert purge gas) and gaseous reaction products, referred to hereinafter as the detector sample, are passed from the outlet port 40 of the probe 10 to the detector 100 through a conduit 90 in fluid communication with the probe 10 and adapted for fluid communication with the detector 100. Preferably, a ¼" (about 6 mm) diameter flexible stainless steel tube conduit 90 is ported into the crystal puller furnace tank above the hot zone insulation package. The transfer of gaseous reaction products from the probe 10 to the detector 100 may be facilitated by means of a vacuum pump 92 having a suction line 93 in fluid communication with the conduit 90. The vacuum pump 92 should preferably be capable of drawing a vacuum of less than about 10 torr (about 1.333 Pa). The suction line 93 can draw from conduit 90 at a point along the conduit which is external to the crystal puller 50 and in relatively closer proximity to the detector 100. The suction line 93 preferably draws from the conduit 90 between first and second detector sample orifices 94, 95 which regulate the sample flow rate to the detector 100. While a single sample orifice configuration can be used, the double sample orifice configuration depicted in FIG. 3 is a preferred system for pressure reduction and is preferably used in conjunction with a continuous flow sample stream bypass. The pressure between the first and second sample orifices 94, 95 is preferably maintained at about 500 mtorr (about 67 Pa) to provide a sufficient pressure differential to transfer the detector sample from the probe 10 through the conduit 90 to the detector 100. An orifice size of about 1 μm can be used in the second sample orifice 95. The size of the first sample orifice is not narrowly critical, but preferably ranges from about 10 μm to about 5 mm. The sample system is preferably regulated to obtain a constant mass flow rate of gas through the probe 10 and a constant pressure between the sample orifices 94, 95. Under such conditions, the detector sample enters the detector 100 with a constant volumetric flow rate.

Suitable detectors 100 for quantifying the amount of a particular gaseous reaction product in the detector sample include mass analyzers and gas-chromatographic detectors, with mass analyzers being preferred. A closed ion source quadrupole gas mass analyzer is a preferred detector 100 for quantifying the amount of $CO(g)$ in a detector sample. Closed ion source quadrupole mass analyzers typically operate at pressures of about $1 \times 10^{-4}$ torr ($1.33 \times 10^{-2}$ Pa) in their ionizing section and at pressures of about $1 \times 10^{-6}$ torr ($1.33 \times 10^{-4}$ Pa) in their detecting section. Where volatile SiO is reacted with carbon according to the preferred reaction and argon is used as the crystal-puller purge gas 58, the detector sample includes unreacted argon, Ar, and $CO(g)$. The quadrupole mass analyzer determines the amount of $CO(g)$ relative to the amount of $^{36}Ar$ (ie., moles CO / moles $^{36}Ar$). $^{36}Ar$ is present in argon at concentrations that are approximately equivalent to the concentration of $CO(g)$ being detected. While the detector 100 preferably detects 100% of the gaseous reaction product present in the detector sample, consistent fractional detection is also suitable for purposes of the present invention. Fractional detection is accounted for, as discussed below, using comparative methodologies or by empirical calibration. Moreover, the relative amount of $CO(g)$ determined may be alternatively expressed in terms of other relative units (e.g., mole fraction, concentration, etc.), or as absolute or temporally related amounts based on a known and regulated detector sample flow rate.

The detector 100 outputs a detector signal (e.g., electrical current, voltage, etc.) which is physically representative of, corresponds to or can be correlated to the amount of reaction product. In the preferred embodiment in which the amount of carbon monoxide gas is quantified using a Quadrupole mass βanalyzer as the detector, the amount of CO present in the sample gas may be determined by admitting a standard gas of 1% CO in Ar to the detector at the same pressure and flow conditions as the sample gas from the SiO probe.

Detector output currents for CO, $I_{28}$, and for $^{36}$Ar, $I_{36}$, are measured for the standard gas and, independently, for the sample gas, and used to quantify the amount of CO in the sample gas according to the following relationship:

$$|\% \text{ CO}|_{sample} = |\% \text{ CO}|_{standard} * \left[ \frac{|I_{28} - I_{28, background}|}{I_{36}} \right]_{sample} * \left[ \frac{I_{36}}{|I_{28} - I_{28, background}|} \right]_{standard}$$

Figure 4:
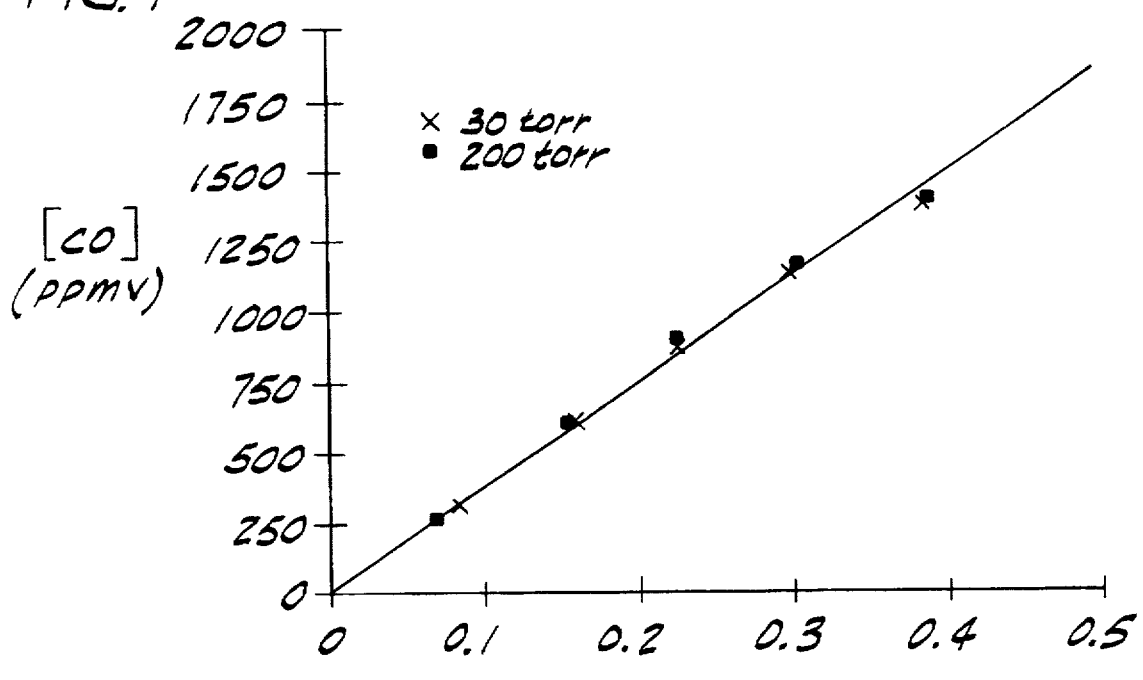
FIG. 4 is a graph which correlates the detector signal, $I_{detector}$ to the amount of gaseous CO reaction product (ppmv in argon purge gas).

$I_{28, background}$ is typically zero. This relationship is preferably calculated using a computer as part of a control system, but could also be calculated manually and/or represented graphically as shown in FIG. 4. (Example 1).

The quantitative relationship between the amount of SiO present in the atmosphere over the molten silicon melt and the signal output from the detector 100 encompasses sampling efficiencies, stoichiometric factors, conversion yields, detection relationships and detection efficiencies. While the exact relationship will vary depending on the type of detector, the relationship may be empirically determined by correlating the detector signal or signals, $I_{detector}$, to known amounts (e.g. concentration) of gaseous reaction product (e.g. CO(g)) in a detector sample gas. (Example 1). As shown in Example 1, where the detector 100 is a quadrupole gas mass analyzer used to quantify the amount of CO formed from reacting SiO with carbon, the output signal is pressure-independent and is proportional to the amount of reaction product detected in the detector sample. Moreover, the amount (e.g. concentration) of reaction product present in the detector sample is equivalent to the amount of reaction product formed, which is related to the amount of SiO reacted by the stoichiometry of the reaction and by the extent of conversion (ie, reaction yield). Hence, the amount of reaction product detected and determined can be quantitatively related to the amount of SiO reacted and, therefore, to the amount of SiO present in the gas sample drawn from the atmosphere over the silicon melt. The amount of SiO present in the atmosphere over the melt may be determined by determining the amount of reaction product formed and then correlating the determined amount of reaction product to the amount of SiO reacted based on stoichiometric and yield considerations. To obtain meaningful comparative data over time, the reaction yield, sampling flow rates and detection efficiencies are preferably maintained constant over time, such that a consistent quantitative relationship exists between the detector signal output from the detector 100 and the amount of SiO reacted. The reaction of SiO and the quantification of the resulting reaction product preferably occurs in less than about 10 minutes, more preferably in less than about 5 minutes and most preferably in less than about 1 minute. Because the crystal pull rate is relatively slow and the advance of a Czochralski crystal during a 5 or 10 minute interval is not substantial, the processes disclosed herein are essentially real-time. The present invention is, however, also intended to encompass reactions and detection schemes which occur less rapidly.

In an independent, but less preferred embodiment, the amount of volatile SiO present in the atmosphere above the melt may be quantified, in real-time or near real-time, using photoabsorbance methods. In this embodiment, a transmitting laser is positioned in the crucible to send an incident beam of light, preferably monochromatic light, through the atmosphere over the silicon melt. The intensity and/or energy level of the incident beam is known. A photoreceptor is positioned in the crucible to receive the beam of light coming through the atmosphere above the melt. The intensity and/or energy of the received beam is determined, and compared to the intensity and/or energy of the incident beam. The difference in intensity and/or energy between the incident and received beams is related to the amount of SiO present in the atmosphere above the melt.

The above described methods for quantifying the amount of volatile SiO over a pool of molten silicon may be used in several practical applications. For example, the quantified amount may be used to determine, in real-time, the amount of oxygen in the molten silicon or in a single crystal silicon ingot being drawn from the molten silicon. After quantifying the amount of SiO present in the atmosphere above the silicon melt, the quantified amount of SiO can be correlated to the amount of oxygen in the melt or, alternatively, in the silicon crystal, using a predetermined empirically-derived correlation. In the preferred embodiment, an analogous correlation can be developed to correlate the amount of reaction product formed (rather than the amount of SiO over the melt) to the amount of oxygen in the molten silicon or to the oxygen content of the single crystal silicon ingot. An empirical correlation between the quantified amount of SiO or the determined amount of reaction product and the oxygen content in the melt or crystal is developed by determining the amount of SiO or the amount of reaction product formed at various known oxygen levels in the melt or crystal. The oxygen content of the melt can be determined by using electrochemical methods known in the art, or alternatively, by determining the oxygen content in a silicon crystal grown from the melt and relating the crystal oxygen content to the melt content through the segregation coefficient (about 1.0). The oxygen content of a silicon crystal can be determined after growth using FTIR spectroscopic techniques or resistivity shift methods. Alternatively, the oxygen content of a crystal can be determined by quantifying the oxygen content in the melt (for example, using electrochemical methods) and relating the melt oxygen content to the crystal content through the segregation coefficient. Once the correlation has been determined, it may be used thereafter to determine or monitor the oxygen content in the melt or crystal in real-time. With reference to FIG. 3, the detector signal from the detector 100 is preferably communicated, directly or indirectly, to a microprocessor 200 (e.g. a personal computer) which has an accessible memory that contains the predetermined correlation for melt and/or crystal oxygen content. The correlation calculation is effected by the microprocessor and the results are displayed, logged and/or put to further use. Potential further use of real-time oxygen-content data includes using the data in a process control scheme or to generate an input signal to alarm circuitry. It is not necessary, however, to effect the correlation calculation for such uses; rather, the uncorrelated detector output signal can itself be used as the input signal to process control or alarm circuitry.

Figure 5:
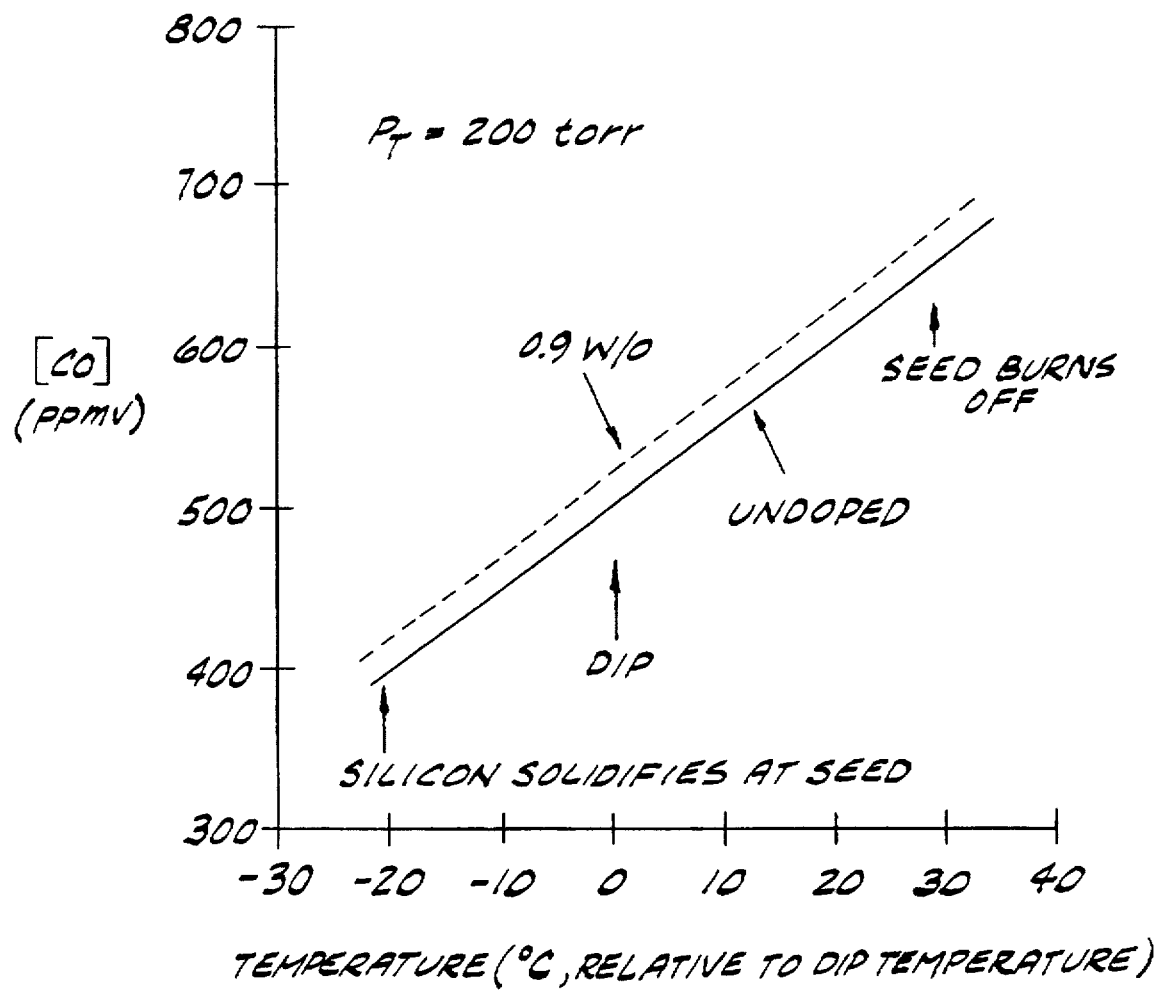
FIG. 5 is a graph which shows how the amount of gaseous CO (ppmv in argon purge gas) reaction product varies with temperature for an undoped silicon melt and for a melt doped with 0.9 wt % antimony.
Figure 6:
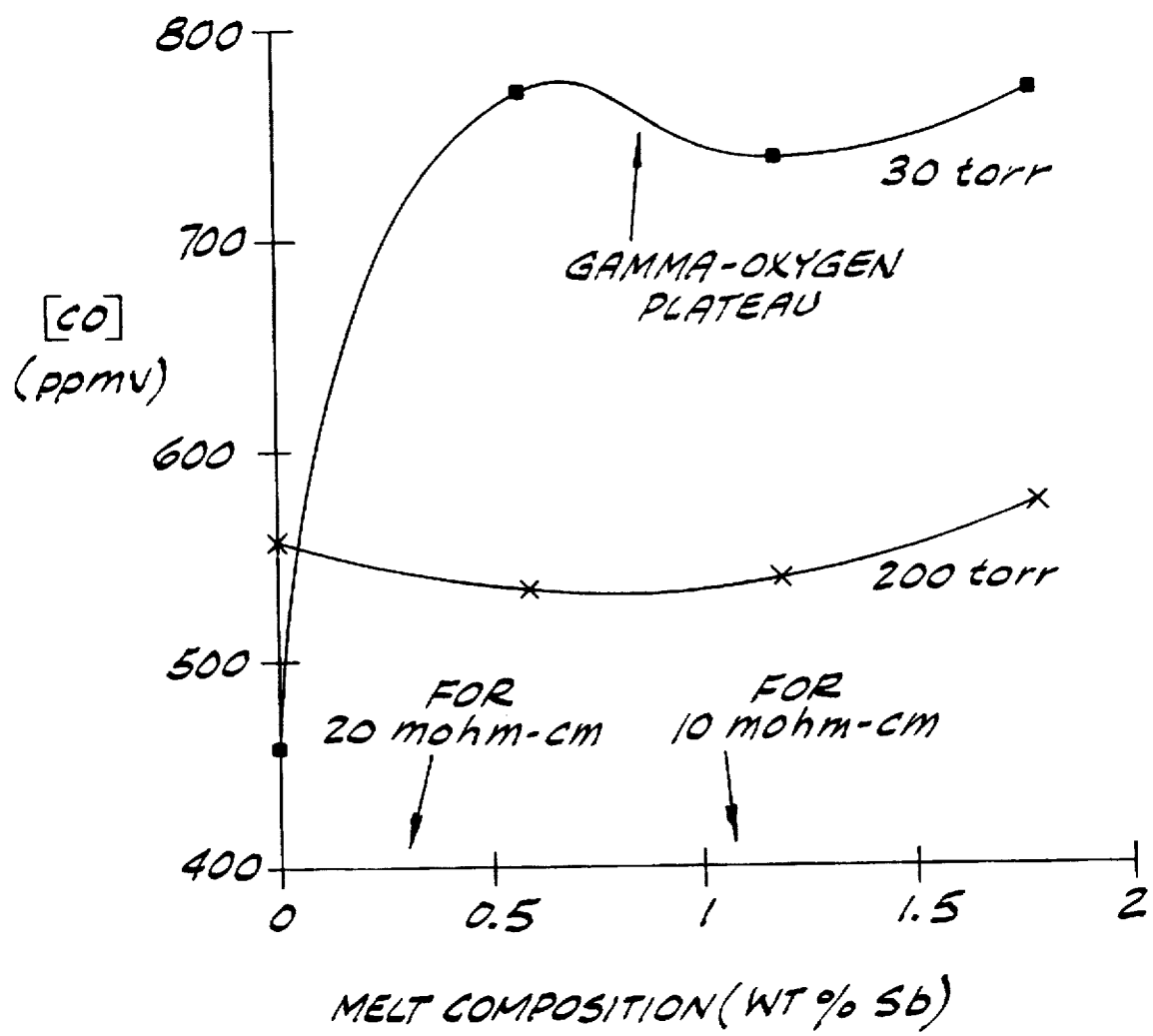
FIG. 6 is a graph which shows how the amount of gaseous CO (ppmv in argon purge gas) reaction product varies with the amount of antimony-dopant in the melt at 30 torr (about 4000 Pa) and at 200 torr (about $2.67 \times 10^4$ Pa).
Figure 7:
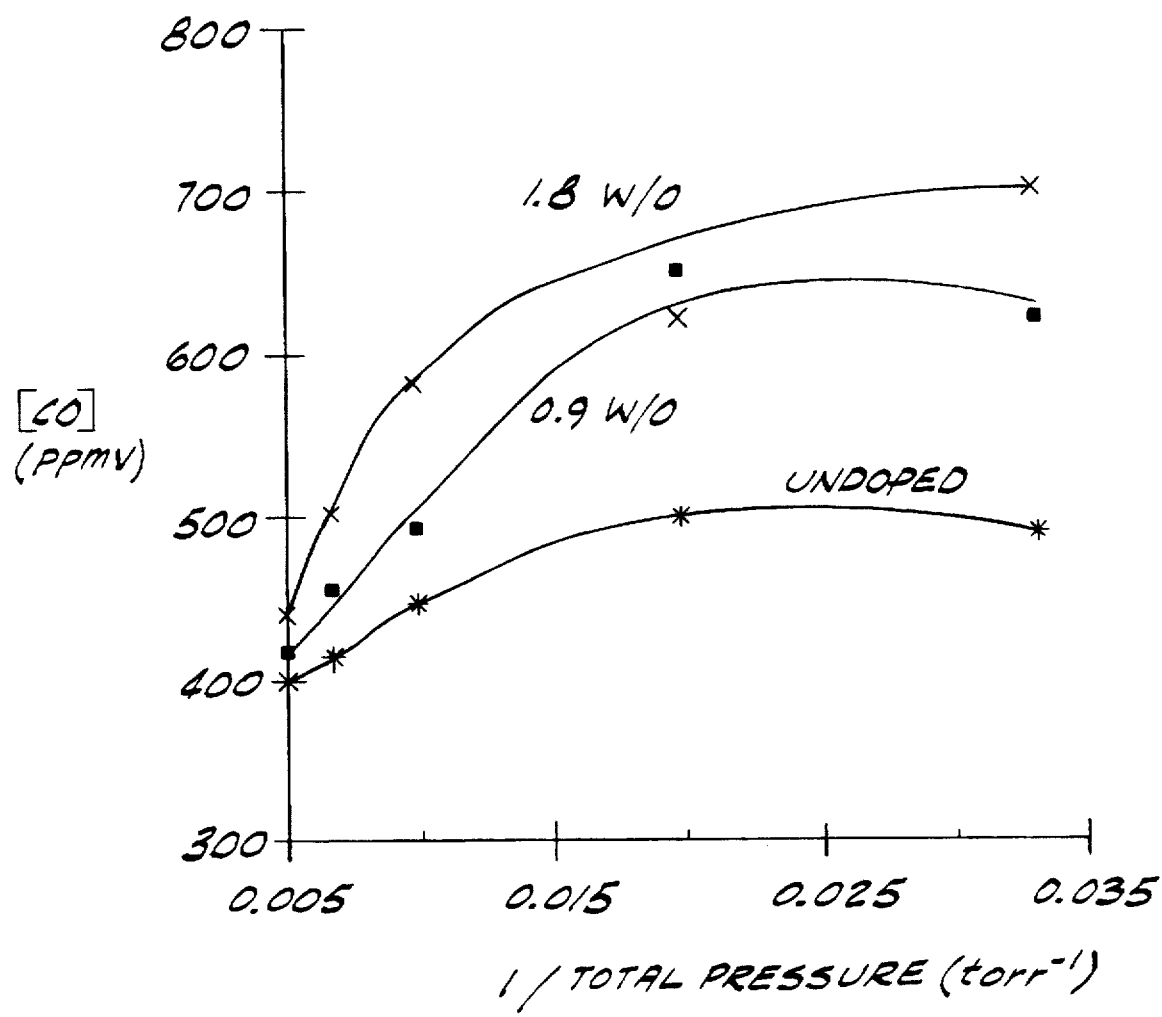
FIG. 7 is a graph which shows how the amount of gaseous CO (ppmv in argon purge gas) reaction product varies with inverse pressure ($torr^{-1}$) for an undoped silicon melt and for melts doped with antimony at a concentration of 0.9 wt % and 1.8 wt %.

The quantified amount of SiO over the melt or the determined amount of reaction product may also be used to monitor real-time changes in the amount of oxygen in the molten silicon and/or the oxygen content in the resulting crystal. For example, it is possible to track how oxygen content in the crystal changes over time. It is also possible to determine how oxygen content changes due to changes in process conditions such as temperature, pressure, dopant concentration, etc. Referring to FIG. 3, the amount of reaction product formed at a given time or for a given process parameter value is determined as described above and the detector signal output from the detector 100 is communicated, directly or indirectly, to the microprocessor 200. The microprocessor 200 may monitor, display, record or further process the detector signal. The change in oxygen content may be monitored in terms of actual oxygen content (e.g. by correlating the detector signal to oxygen content using a predetermined calibration as described above) or in proportional terms (e.g. in terms of the detector signal, $I_{detector}$, representing the amount of reaction product formed). A monitoring system which includes a SiO probe 10, a detector 100 and a microprocessor 200 may be used according to the method disclosed herein to evaluate the effects of temperature, pressure and antimony dopant concentration on oxygen content in a silicon crystal. (Example 2; FIGS. 5, 6 and 7).

Changes in oxygen content over time, in actual or proportional terms, can also be used to control, in near real-time, the oxygen content in a single crystal silicon ingot being drawn from a silicon melt. (Example 3). Such control can be effected manually by observing the quantified amount of SiO or the determined amount of reaction product formed, and then manually adjusting a process condition that affects oxygen content in the crystal. However, such control is preferably effected using an automated, closed-loop control system. While the particular type of control system used is not narrowly critical, the quantified amount of SiO over the melt or the determined amount of reaction product formed is preferably used in a feedback or inferential control system based on the relationship between the amount of SiO above the melt or the amount of reaction product formed and the oxygen content of the growing crystal at the melt/crystal interface. The particular control configuration is also not narrowly critical; changes in one or more of a variety of process conditions which affect oxygen content in the silicon crystal may be effected based on the quantified amount of SiO or based on the determined amount of reaction product.

With reference to FIG. 3, the amount of volatile SiO is quantified using the SiO reaction probe 10 and detector 100 as described above. The resulting detector signal is representative of the amount of reaction product formed and can be quantitatively related to the amount of SiO over the melt. The detector signal is preferably used in the control system as an indirect (secondary) measurement of the oxygen content of the growing crystal. The detector signal is preferably transmitted or otherwise communicated, directly or indirectly (e.g. through a microprocessor 200), to a controller 300. Any standard controller may be employed, including for example, analog proportional (P), proportional-integral (PI) or proportional-integral-derivative (PID) controllers, digital controllers approximating such analog P, PI or PID controllers, or more sophisticated digital controllers. A digital PID controller is preferred. Such a digital controller 300 can itself comprise a microprocessor, or can comprise a portion of a larger microprocessor 200. The controller 300 may also communicate, directly or indirectly, with a separate microprocessor 200 to provide user input to the controller, data collection, alarm indications, process control tracking, etc. The controller 300 (or microprocessor 200) may modify the received detector signal for use in calculating the necessitated change in process conditions, for user-interface or for data acquisition or display. For example, the controller 300 (or microprocessor 200) may relate the detector signal to the actual oxygen content of the growing crystal using a predetermined empirical or theoretical correlation. Additionally or alternatively, the received detector signal may be converted into a differential signal generated by comparing the detector signal with a prescribed setpoint value and/or with a subsequently received detector signal. In the latter case, real-time changes in oxygen content of the single crystal silicon ingot are detected as the ingot is drawn from a silicon melt by quantifying the amount of SiO present in an atmosphere above the silicon melt at a first time $t_1$, and at a later time $t_2$. The detector signals which are output from the detector 100 at times $t_1$ and $t_2$ are communicated to the controller 300 (or microprocessor 200) for comparison and generation of the differential signal. The controller 300 may modify the received detector signal by means of its own integrated control-microprocessor, or alternatively, the system microprocessor 200 may effectuate such modifications and communicate the modified signal to the controller for generation of a control signal.

The controller 300 generates a control signal based on the detector signal (either as received from the detector 100 or as modified by the microprocessor 200 or controller 300). In typical applications, the controller converts the detector signal or differential signal generated therefrom to a control signal by applying a control law which relates the process condition to be changed to the resulting effect of such a change on the oxygen content of the crystal. The control law may be based on theoretical and/or empirical considerations. The control law used in a particular situation varies depending on the process condition being changed and on the type of process control element being manipulated for implementing the change in process condition. The control signal generated by the controller 300 may be of a variety of types (e.g. pneumatic or electrical signals), and can be transmitted or otherwise communicated, directly or indirectly, to a process control element 400 which changes at least one process condition that affects oxygen content in the silicon crystal. A control signal can also be communicated to the process control element 400 via the microprocessor 200 (dashed line in FIG. 3).

Process conditions affecting oxygen content are known in the art. The concentration of oxygen in the molten silicon is a primarily a function of the melt temperature, the extent of circulation of molten silicon within the crucible, and the total pressure in the crystal puller. The crucible-melt interface temperature and the circulation of the melt each affect the supply of oxygen through diffusion from the $SiO_2$ crucible into the bulk of the molten silicon. The loss of oxygen from the molten silicon occurs primarily through evaporation of SiO at the surface of the melt; the crystal removes comparatively little oxygen. While the evaporation rate is dependent upon the concentration of oxygen in the melt, the partial pressure of SiO over the melt, and the total pressure, the partial pressure of SiO is small in a CZ system using a purge gas, and therefore, the total pressure is a significant factor affecting loss of oxygen. Hence, the process conditions which can be manipulated to effect a change in oxygen content of the molten silicon and/or the silicon ingot include the temperature profile of the hot zone (U.S. Pat. No. 4,511,428 to Ghosh et al.); the crucible 56 rotation rate (U.S. Pat. No. 4,436,577 to Frederick et al.); modulation of the crucible rotation rate; the strength and location of an applied magnetic field (Japanese Kokai Patent No. Sho 58[1983]-217493, WO 89/08731 to Barraclough et al., Japanese Kokai Patent No.'s Hei 1[1989]-282185 and Hei 2[1990]-55284 to Hirata et al., U.S. Pat. No. 5,178,720 to Frederick); the pull rate of the crystal 55; the partial pressure of oxygen or inert gasses (e.g. nitrogen, argon) over the melt surface 53 (U.S. Pat. No. 4,400,232 to Ownby et al., U.S. Pat. No. 4,591,409 to Ziem et al.); the total pressure in the crystal puller 50 (U.S. Pat. No. 5,131,974 to Oda et al.); and the flow rate of inert purge gas 58 (U.S. Pat. No. 5,131,974 to Oda et al.). The control system of the present invention encompasses these and other process conditions which affect oxygen content, whether known presently or developed in the future. The process conditions affecting oxygen content may be controlled individually or jointly, and simultaneously or sequentially, by a variety of control elements 400 known in the art. Exemplary process control elements 400 include valves, relay switches, rheostats, SCR's and other power supply controllers, variable speed motors, variable speed pumps, variable speed compressors, etc. When the process control element 400 receives the control signal, the corresponding process condition is preferably controlled by manipulating the control element 400 to bring the real-time oxygen content closer to a desired value. The sense (e.g. increase or decrease) and magnitude of the change in process condition is based, through the design of the control element 400, on the control signal received from the controller or microprocessor, and is thus also based on the quantified amount of SiO present over the melt or on the determined amount of reaction product formed by reacting SiO in the probe.

The following examples illustrate the principles and advantages of the invention.

EXAMPLES

Example 1
Calibration of Detector Signal, $I_{detector}$, to Concentration of CO(g) Reaction Product Gas mixtures comprising gaseous carbon monoxide and argon at various known concentrations of CO(g) were prepared from a source gas having 1% CO, by weight, in argon. The gas mixtures were metered at about 1–5 standard liters per minute into a cold crystal puller at 30 torr (about 4000 Pa) and at 200 torr (about $2.67 \times 10^4$ Pa). Argon purge rate was about 66.1 scfh (about 0.52 liters/sec). The crystal puller was equipped with an SiO probe loaded with graphite wool reactant, and the detector samples were passed through the probe to a quadrupole mass analyzer through a conduit equipped with a vacuum pump. The detector pressure was about $4 \times 10^{-5}$ torr (about $5.33 \times 10^{-3}$ Pa). The detector signal output, $$I_{detector} = \frac{I_{28} - I_{28} \text{ (background)}}{I_{36}},$$

(where $I_{28}$ and $I_{36}$ refer to the current (amps) generated for CO(g) and for $^{36}$Ar, respectively) was determined for the various concentrations of CO(g), as shown in FIG. 4. The detector signal was proportional to the amount of CO(g) in the detector sample gas and was independent of pressure.

Example 2
Effect of Melt Temperature, Pressure and Antimony—Dopant Concentration on Oxygen Content of CZ Silicon Crystal A monitoring system which included a SiO probe 10, a detector 100 and a microprocessor 200 (FIG. 3) were used to evaluate the effects of temperature, pressure and antimony-dopant concentration on SiO evaporation from the silicon melt. In the experiments, a 14 inch quartz crucible containing 26 kg molten silicon was rotated at 4 rpm. An argon purge of about 66.1 scfh (about 0.52 liters/sec) was established and maintained. Gaseous SiO reacted with graphite wool reactant in the probe 10 to form SiC and carbon monoxide gas. The amount of carbon monoxide formed was determined using a quadrupole gas mass analyzer detector 100. The detector signal was correlated to concentration (ppmv) of carbon monoxide, based on the empirical calibration as set out in FIG. 4 (Example 1).

In a first set of experiments, the effect of temperature on SiO evaporation was determined for undoped and antimony-doped (0.9 wt %) silicon melts. FIG. 5 shows the concentration of reaction product (ppmv CO) versus temperature (heater setpoint temperature in °C, relative to the dip temperature) at a constant total pressure of about 200 torr (about $2.67 \times 10^4$ Pa). As shown therein, evaporation of SiO increases with increasing temperature (due to an increase in oxygen concentration in the melt), but only a slight change in SiO evaporation is observed when antimony is added to the melt at this pressure.

Another set of experiments investigated the effect of dopant concentration on SiO evaporation at different pressures. FIG. 6 shows how the concentration of reaction product (ppmv CO) varied with the concentration of antimony in the melt (weight percent Sb) at total pressures of 30 torr (about 4000 Pa) and 200 torr (about $2.67 \times 10^4$ Pa). The data shown in FIG. 6 suggests that the amount of oxygen in the molten silicon (and, therefore, the oxygen content of a crystal drawn from the melt) was relatively independent of antimony concentration at higher pressures, as compared to the dependence at lower pressures.

A further set of experiments considered the effect of pressure on SiO evaporation for melt compositions having different antimony concentrations. FIG. 7 shows how the concentration of reaction product (ppmv CO) varies with inverse total pressure (torr$^{-1}$) for an undoped silicon melt and for melt compositions having 0.9 wt. % and 1.8 wt. % antimony. This data further suggests that the effect of antimony-dopant concentration on oxygen content is minimized at higher pressures relative to lower pressures.

Example 3
Use of SiO Probe for Oxygen Control During CZ Crystal Growth

Two crystals were produced from a 26 kg charge formed in a 14" diameter crucible using a crystal rotation of 15 rpm CCW with a crucible rotation of 8 rpm CW. For each crystal, the melt surface position was 60 mm below the top of the heater and maintained at that level for the duration of crystal growth. The initial furnace pressure was 30 torr with an argon flow of 135 scfh (60 slm). The target pull rate profile was approximately:

pull rate (mm/min)=1+0.8 exp[Length(mm) /150 (mm)].

During growth of the first crystal, the total pressure was maintained constant at 30 torr, without controlling any of the process conditions that affect oxygen content. During growth of the second crystal, a sample containing SiO was drawn into a SiO reaction probe from the atmosphere over the molten silicon using the system configuration shown in FIG. 2(*a*). The SiO was reacted with graphite wool in the probe to form CO gas, and the amount of CO formed was determined (concentration of CO in argon) by a quadrupole mass analyzer. As the second crystal was grown, the total furnace absolute pressure was increased to maintain the determined concentration of CO below 550 ppmv. The preferred 550 ppmv upper limit on the concentration of CO was established based on the results of the investigation in Example 2 related to FIG. 6. The total furnace absolute pressure was increased during growth by throttling down (that is, decreasing the opening setting) on the furnace's exhaust throttle valve, a butterfly-type gas throttle valve.

Figure 8:
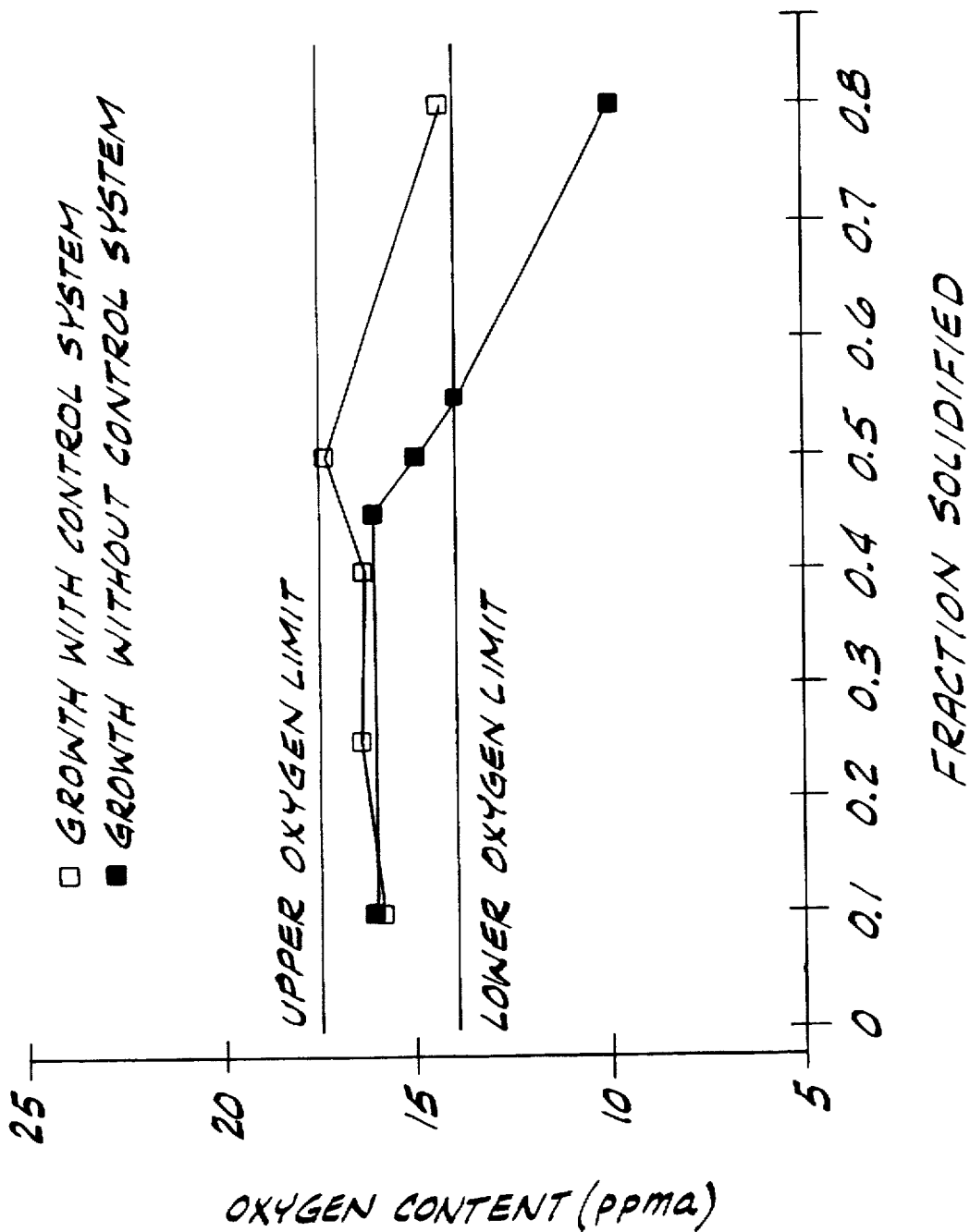
FIG. 8 is a graph which shows the oxygen content of a silicon crystal over the length thereof for crystals grown with and without the control system of the present invention.

As shown in FIG. 8, the oxygen content of the first crystal (closed squares) was below the desired lower oxygen limit for about 42% of the crystal. However, the oxygen content of the second crystal (open squares) remained within the desired limits over the entire length of the crystal.

In light of the detailed description of the invention and the examples presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

I claim:

1. A method for determining the amount of SiO present in an atmosphere over a pool of molten silicon, the method comprising withdrawing a sample containing SiO from the atmosphere over the pool of molten silicon, reacting SiO present in the sample with a reactant to form a detectable reaction product, determining the amount of reaction product formed, and correlating the determined amount of reaction product to the amount of SiO present in the atmosphere.

2. The method of claim 1 wherein the reaction product is a gaseous reaction product which is detectable at ambient temperature.

3. The method of claim 1 wherein the reactant is a carbon-containing material and at least one reaction product is carbon monoxide gas.

4. The method of claim 1 wherein the SiO present in the atmosphere over the molten silicon is reacted with graphite to form carbon monoxide gas and silicon carbide.

5. The method of claim 1 wherein the time elapsed between the step of withdrawing the sample and the step of determining the amount of reaction product formed is less than about 5 minutes.

6. The method of claim 1 wherein the sample containing SiO is withdrawn into a reaction probe that includes a graphite reactant, the SiO present in the sample is reacted with graphite in the probe to form carbon monoxide gas and silicon carbide, the amount of carbon monoxide formed is determined using a quadrupole gas mass analyzer, and the determined amount of carbon monoxide is correlated to the amount of SiO present in the atmosphere over the pool.

7. A method for determining the amount of oxygen in a pool of molten silicon, the method comprising quantifying the amount of SiO present in an atmosphere over the pool of molten silicon, and correlating the quantified amount of SiO to the amount of oxygen in the molten silicon.

8. The method of claim 7 wherein the amount of SiO present in the atmosphere over the pool is quantified by withdrawing a sample containing SiO from the atmosphere, reacting SiO present in the sample with a reactant to form a detectable reaction product, determining the amount of reaction product formed, and correlating the determined amount of reaction product to the amount of SiO present in the atmosphere.

9. A method for determining the amount of oxygen in a pool of molten silicon, the method comprising withdrawing a sample containing SiO from an atmosphere over the molten silicon, reacting SiO present in the sample with a reactant to form a detectable reaction product, determining the amount of reaction product formed, and correlating the determined amount of reaction product to the amount of oxygen in the pool of molten silicon.

10. A method for determining, in near real-time, the oxygen content in a single crystal silicon ingot being drawn from a pool of molten silicon, the method comprising quantifying the amount of SiO present in an atmosphere over the pool of molten silicon, and correlating the quantified amount of SiO to the oxygen content in the single crystal silicon ingot.

11. The method of claim 10 wherein the amount of SiO present in the atmosphere over the pool is quantified by withdrawing a sample containing SiO from the atmosphere, reacting SiO present in the sample with a reactant to form a detectable reaction product, determining the amount of reaction product formed, and correlating the determined amount of reaction product to the amount of SiO present in the atmosphere.

12. A method for determining, in near real-time, the oxygen content in a single crystal silicon ingot being drawn from a pool of molten silicon, the method comprising withdrawing a sample containing SiO from an atmosphere over the pool of molten silicon, reacting SiO present in the sample with a reactant to form a detectable reaction product, determining the amount of reaction product formed, and correlating the determined amount of reaction product to the oxygen content in the single crystal silicon ingot.

13. A method for controlling, in near real-time, the oxygen content in a single crystal silicon ingot being drawn from a pool of molten silicon under a set of process conditions that affect the oxygen content in the ingot, the method comprising quantifying the amount of SiO present in an atmosphere over the pool of molten silicon while the silicon ingot is being drawn, and effecting a change in at least one process condition that affects the oxygen content in the silicon ingot, the sense and magnitude of the change being based on the quantified amount of SiO present in the atmosphere.

14. The method of claim 13 wherein the amount of SiO present in the atmosphere over the pool is quantified by withdrawing a sample containing SiO from the atmosphere, reacting SiO present in the sample with a reactant to form a detectable reaction product, determining the amount of reaction product formed, and correlating the determined amount of reaction product to the amount of SiO present in the atmosphere.

15. A method for controlling, in near real-time, the oxygen content in a single crystal silicon ingot being drawn from a pool of molten silicon under a set of process conditions that affect the oxygen content in the ingot, the method comprising withdrawing a sample containing SiO from an atmosphere over the pool of molten silicon, reacting SiO present in the sample with a reactant to form a detectable reaction product, determining the amount of reaction product formed, and effecting a change in at least one process condition that affects the oxygen content in the silicon ingot, the sense and magnitude of the change being based on the determined amount of reaction product.

16. The method of claim 15 wherein the change in at least one process condition affecting the oxygen content is effected by communicating the determined amount of reaction product to an automated control system capable of controlling at least one process condition that affects the oxygen content in the ingot and using the control system to effect the change, the sense and magnitude of the change being based on the determined amount of reaction product communicated to the control system.

17. The method of claim 15 wherein the reaction product is a gaseous reaction product which is detectable at ambient temperature.

18. The method of claim 15 wherein the reactant is a carbon-containing material and at least one reaction product is carbon monoxide gas.

19. The method of claim 15 wherein the SiO present in the atmosphere over the molten silicon is reacted with graphite to form carbon monoxide gas and silicon carbide.

20. The method of claim 15 wherein the time elapsed between the step of withdrawing the sample and the step of using the control system to effect a change in at least one process condition that affects the oxygen content is less than about 10 minutes.

21. The method of claim 15 wherein the control system is used to effect a change in a process condition selected from the group consisting of crucible rotation rate, crucible rotation rate modulation, magnetic field strength and magnetic field location.

22. A probe for use in reacting SiO present in a gas sample withdrawn from an atmosphere over a pool of molten silicon with a reactant to form a detectable reaction product, the probe being suitable for use in a system for determining or controlling, in near-real time, the amount of SiO present in the atmosphere over the molten silicon, the amount of oxygen in the molten silicon or the oxygen content of a single crystal silicon ingot drawn from the molten silicon, the probe comprising a reaction chamber defined in a body of the probe, the probe body being made of a material having a melting point greater than about 1500° C. and being non-contaminating to the molten silicon when positioned over the pool of molten silicon, an inlet port in fluid communication with the chamber and adapted for fluid communication with the atmosphere for withdrawing a sample containing SiO from the atmosphere into the chamber, and an outlet port in fluid communication with the chamber and adapted for fluid communication with a detector for determining the amount of reaction product formed.

23. The SiO probe of claim 22 further comprising a reactant material contained within the chamber, the reactant material being capable of reacting with SiO present in the sample drawn into the chamber through the inlet port to form a detectable reaction product.

24. The SiO probe of claim 23 wherein the reactant material is graphite.

25. The SiO probe of claim 22 further comprising means for supplying a reactant in the chamber to react with SiO to form a reaction product.

26. A system for use in determining or controlling, in near-real time, the amount of SiO present in an atmosphere over a pool of molten silicon contained within a quartz crucible, the amount of oxygen in the molten silicon or the oxygen content of a single crystal silicon ingot drawn from the molten silicon according to the Czochraski method, the system comprising a SiO reaction probe located within a Czochraski crystal puller in the atmosphere over the pool of molten silicon for reacting SiO present in a gas sample withdrawn from the atmosphere with a reactant to form a detectable reaction product, the probe comprising a reaction chamber defined in a body of the probe, the probe body being made of a material having a melting point greater than about 1500° C. and being non-contaminating to the molten silicon, an inlet port in fluid communication with the chamber and adapted for fluid communication with the atmosphere for withdrawing a sample containing SiO from the atmosphere into the chamber, an outlet port in fluid communication with the chamber and adapted for fluid communication with a detector for determining the amount of reaction product formed, and a reactant material contained within the chamber, the reactant material being capable of reacting with SiO present in the sample drawn into the chamber through the inlet port to form a detectable reaction product, and a detector for determining the amount of reaction product formed.

27. The system of claim 26 wherein the reaction product formed is a gas detectable at ambient temperature, the system further comprising a conduit in fluid communication with the probe and adapted for fluid communication with the detector to pass the gaseous reaction product from the probe to the detector, the detector being located outside of the crystal puller.

28. The system of claim 26 further comprising a controller for receiving a signal generated by the detector, the signal being representative of the determined amount of reaction product and being received by the controller directly from the detector or indirectly therefrom via a microprocessor, the controller generating a control signal based on the signal received, and a process control element for receiving the control signal, the control signal being received directly from the controller or indirectly therefrom via a microprocessor, the process control element effecting a change in at least one process condition that affects the oxygen content in the silicon ingot, the sense and magnitude of the change being based on the control signal.

29. A method for determining, in near real-time, the oxygen content in a single crystal silicon ingot being drawn from a pool of molten silicon, the method comprising withdrawing a sample containing SiO from an atmosphere over the pool of molten silicon, reacting SiO present in the sample with graphite to form gaseous carbon monoxide and SiC, determining the amount of carbon monoxide formed, and correlating the determined amount of carbon monoxide to the oxygen content in the single crystal silicon ingot.

30. The method of claim 29 wherein the sample containing SiO is withdrawn into a reaction probe that includes the graphite reactant, the amount of carbon monoxide formed is determined using a quadrupole gas mass analyzer, and the time elapsed between the step of withdrawing the sample and the step of determining the amount of carbon monoxide formed is less than about 1 minute.

* * * * *